(12) United States Patent
Criniere et al.

(10) Patent No.: US 8,876,926 B2
(45) Date of Patent: Nov. 4, 2014

(54) LIQUID SUSPENSIONS AND POWDERS OF CERIUM OXIDE PARTICLES AND PREPARATION AND POLISHING APPLICATIONS THEREOF

(75) Inventors: Guillaume Criniere, Ixelles (BE); Laurent Thiers, Savigny-sur-Orge (FR)

(73) Assignee: Rhodia Operations, Aubervilliers (FR)

( * ) Notice: Subject to any disclaimer, the term of this patent is extended or adjusted under 35 U.S.C. 154(b) by 636 days.

(21) Appl. No.: 13/058,771

(22) PCT Filed: Jul. 7, 2009

(86) PCT No.: PCT/EP2009/058571
§ 371 (c)(1), (2), (4) Date: May 12, 2011

(87) PCT Pub. No.: WO2010/020466
PCT Pub. Date: Feb. 25, 2010

(65) Prior Publication Data
US 2011/0225897 A1    Sep. 22, 2011

(30) Foreign Application Priority Data

Aug. 22, 2008 (FR) .................... 08 04676

(51) Int. Cl.
| | |
|---|---|
| B24D 3/02 | (2006.01) |
| C09C 1/68 | (2006.01) |
| C09K 3/14 | (2006.01) |
| C09G 1/02 | (2006.01) |
| B82Y 30/00 | (2011.01) |
| C01F 17/00 | (2006.01) |

(52) U.S. Cl.
CPC ........... *C09K 3/1436* (2013.01); *C01P 2004/03* (2013.01); *C09G 1/02* (2013.01); *B82Y 30/00* (2013.01); *C01P 2004/62* (2013.01); *C09K 3/1472* (2013.01); *C09K 3/1463* (2013.01); *C01P 2006/22* (2013.01); *C01P 2004/52* (2013.01); *C01F 17/0043* (2013.01); *C01P 2006/12* (2013.01); *C01P 2004/64* (2013.01); *C01P 2004/50* (2013.01)
USPC ................................. 51/307; 51/308; 51/309

(58) Field of Classification Search
USPC .................................................... 51/307–309
See application file for complete search history.

(56) References Cited

U.S. PATENT DOCUMENTS

| | | | |
|---|---|---|---|
| 6,706,082 B2 | 3/2004 | Ota et al. | |
| 8,317,888 B2 * | 11/2012 | Criniere | ......................... 51/307 |
| 2010/0072417 A1 * | 3/2010 | Criniere | ....................... 252/79.1 |

FOREIGN PATENT DOCUMENTS

| | | |
|---|---|---|
| EP | 1234801 A2 | 8/2002 |
| WO | WO 2008/043703 A2 | 4/2008 |

OTHER PUBLICATIONS

International Search Report corresponding to PCT/EP 2009/058571 mailed Oct. 6, 2009.

*Primary Examiner* — Shuangyi Abu Ali
(74) *Attorney, Agent, or Firm* — Dentons US LLP

(57) ABSTRACT

Suspensions of cerium oxide particles, well suited for polishing applications, the particles (secondary particles) of which have an average size of at most 200 nm, these secondary particles are formed from primary particles whose average size measured by TEM is at most 150 nm with a standard deviation of at most 30% of the value of this average size, and for which the ratio of the average size measured by TEM to the average size measured by BET is at least 1.5. Such suspensions are prepared from solutions of a cerium III salt, comprising a colloidal dispersion of cerium IV, which are contacted, in the presence of nitrate ions and under an inert atmosphere, with a base, and the medium obtained is subjected to a thermal treatment under an inert atmosphere and then acidified and washed.

5 Claims, 1 Drawing Sheet

LIQUID SUSPENSIONS AND POWDERS OF CERIUM OXIDE PARTICLES AND PREPARATION AND POLISHING APPLICATIONS THEREOF

CROSS-REFERENCE TO PRIORITY/PCT APPLICATIONS

This application is a national phase of PCT/EP 2009/058571, filed Jul. 7, 2009 and designating the United States (published in the French language on Feb. 25, 2009, as WO 2009/020466 A1; the title and abstract were also published in English), which claims foreign priority under 35 U.S.C. §119 of FR 0604676, filed Aug. 22, 2008, each hereby expressly incorporated by reference in its entirety and each assigned to the assignee hereof.

The present invention relates to a liquid suspension and a powder of cerium oxide particles, to processes for the preparation thereof and to the use thereof in particular in polishing.

The development of the electronics industry requires the increasingly considerable use of compositions for polishing various parts such as discs or dielectric compounds. These compositions are in the form of suspensions and they must correspond to a certain number of characteristics. For example, they must offer a high degree of removal of material, which reflects their abrasive capacity. They must also have a defectuosity which is as low as possible; the term "defectuosity" is intended to mean in particular the amount of scratches exhibited by the substrate once treated with the composition.

For reasons of stability and of ease of use, these suspensions must consist of particles of submicronic dimension, i.e. generally less than 300 nm. In addition, the presence of particles that are too fine in these suspensions reduces their abrasive capacities. Moreover, particles that are too large can contribute to an increase in the defectuosity. There is therefore a need for suspensions in which the particles are monodisperse. It should also be noted that, in order to obtain optimal performance levels, this monodispersity should apply both to the primary particles and to the secondary particles, i.e. the aggregates consisting of the primary particles.

Finally, it may be advantageous, in order to improve the polishing capacities, to have suspensions for which the particles which have an identical size compared with those of other suspensions, nevertheless have a larger specific surface area.

It is thus understood that the development of these suspensions is a complex problem.

The object of the invention is to provide suspensions which correspond to the conditions described above, i.e. suspensions in which the particles are monodisperse and optionally have an improved specific surface area.

With this aim, the suspension of the invention is a suspension of cerium oxide particles in a liquid phase, and it is characterized in that these particles (secondary particles) have an average size of at most 200 nm, these secondary particles consisting of primary particles whose average size measured by TEM is of at most 150 nm with a standard deviation of at most 30% of the value of said average size, and for which the ratio of the average size measured by TEM to the average size measured by BET is at least 1.5.

Other characteristics, details and advantages of the invention will emerge even more fully upon reading the description which follows, the concrete but nonlimiting examples intended to illustrate it, and the attached drawing in which.

Figure 1:
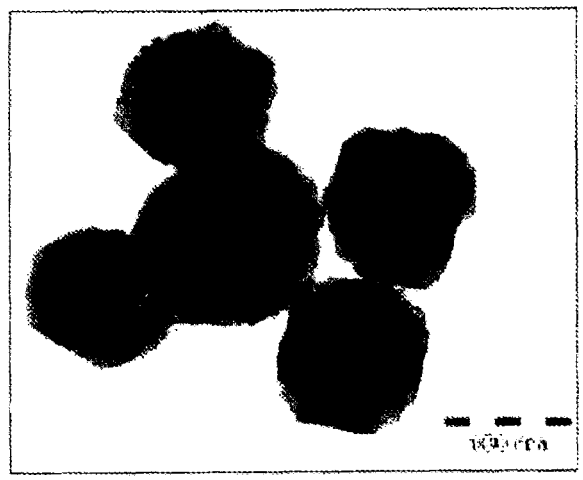
FIG. 1 is a TEM photograph of a suspension according to the invention.

For the remainder of the description, the expression "suspension of cerium oxide particles" denotes a system consisting of solid fine particles of submicronic dimension based on this oxide, stably dispersed in a liquid phase, it being possible for said particles to also optionally contain residual amounts of bound or adsorbed ions such as, for example, nitrates or ammoniums.

Still for the remainder of the description, the term "specific surface area" is intended to mean the B.E.T. specific surface area determined by nitrogen adsorption in accordance with standard ASTM D 3663-78 established based on the Brunauer-Emmett-Teller method described in the periodical "The Journal of the American Chemical Society, 60, 309 (1938)". Finally, "TEM" is intended to mean transmission electron microscopy.

The particles of the suspension are based on cerium oxide which is generally crystalline ceric oxide.

The particles which constitute the suspension of the invention and which have an average size of at most 200 nm are called, in the remainder of the description, "secondary particles". These particles are aggregates aggregated from other, finer particles, subsequently called "primary particles".

According to an important characteristic of the invention, these primary particles are fine and monodisperse. They in fact have an average size measured by TEM of at most 150 nm with a standard deviation of at most 30% of the value of the average size of these primary particles.

The standard deviation mentioned in the present invention and measured also by implementing the TEM technique has the usual mathematical meaning, it is the square root of the variance and it is expressed by the formula:

$$\sigma = \sqrt{\frac{1}{n}\sum_{i=1}^{n}(x_i - \bar{x})^2}$$

n being the number of particles taken into account in the measurement,
$x_i$ being the size of a particle i,
$\bar{x}$ being the average value of the size of the particles ($1/n\Sigma_i x_i$).

The size of the n various particles is measured using a photograph obtained by TEM.

This standard deviation can be preferably of at most 20%, more particularly at most 15%, of the value of the average size of the primary particles.

The primary particles can more particularly have sizes which exhibit an average value of at most 130 nm.

These average sizes of primary particles can, moreover, be at least 50 nm, in particular at least 80 nm, and more particularly at least 100 nm.

Another characteristic of the primary particles of the suspension according to the invention is the ratio of the average size thereof measured according to various techniques.

More specifically, and as indicated above, the ratio of the average size measured by TEM to the average size measured by BET is at least 1.5. This ratio may be at least 2.

The expression "average size measured by BET" is intended to mean the theoretical size obtained from the value of specific surface area measured by the BET technique and assuming a nonporous spherical particle of $CeO_2$ having a density of 7.2.

Without wishing to be bound by a theory, the fact that the ratio of the sizes is other than 1 may reflect surface defects in the particles, the surface of said particles appearing less wellfaceted than in known products. These defects may result in an increase in the specific surface area of the particles.

As indicated above, the primary particles form aggregates which thus constitute the secondary particles. These secondary particles can more particularly have an average size of at most 150 nm, more particularly of at most 120 nm and even more particularly of at most 100 nm.

Moreover, according to another advantageous characteristic of the invention, these secondary particles are themselves also monodisperse. They can in fact have a dispersion index of at most 0.5. This index can be in particular of at most 0.4, more particularly at most 0.3 and even more particularly at most 0.2.

For the entire description regarding the secondary particles, the average size and the dispersion index are the values obtained by implementing the laser diffraction technique using a laser particle sizer (distribution by volume).

The term "dispersion index" is intended to mean the ratio:

$$\sigma/m = (d_{90} - d_{10})/2d_{50}$$

in which:
- $d_{90}$ is the particle size or diameter for which 90% of the particles have a diameter of less than $d_{90}$;
- $d_{10}$ is the particle size or diameter for which 10% of the particles have a diameter of less than $d_{10}$;
- $d_{50}$ is the average size or diameter of the particles.

The liquid phase of the suspensions according to the invention may be of various nature.

It can first of all be water.

It can also be a water/water-miscible solvent mixture. As an example of a solvent of this type, mention may be made of alcohols such as methanol or ethanol, glycols such as ethylene glycol, acetate derivatives of glycols, such as ethylene glycol monoacetate, or polyols.

Finally, the liquid phase can consist of an organic solvent.

As an example of an organic solvent, mention may be made of aliphatic hydrocarbons such as hexane, heptane, octane or nonane, inert cycloaliphatic hydrocarbons such as cyclohexane, cyclopentane or cycloheptane, aromatic hydrocarbons such as benzene, toluene, ethylbenzene, xylenes, or liquid naphthenes. Also suitable are petroleum fractions of the Isopar or Solvesso type (trade marks registered by the company Exxon), in particular Solvesso 100 which contains essentially a mixture of methylethylbenzene and trimethylbenzene, Solvesso 150 which contains a mixture of alkylbenzenes, in particular of dimethylbenzene and of tetramethylbenzene, and Isopar which contains essentially $C_{11}$ and $C_{12}$ isoparaffinic and cycloparaffinic hydrocarbons. Other types of petroleum fractions that may also be mentioned include those of Petrolink® type from the company Petrolink or of Isane® type from the company Total.

Chlorinated hydrocarbons, such as chlorobenzene, dichlorobenzene or chlorotoluene, can also be used as organic solvent. Aliphatic and cycloaliphatic ethers or ketones, for instance diisopropyl ether, dibutyl ether, methyl ethyl ketone, methyl isobutyl ketone, diisobutyl ketone or mesityl oxide, can be envisaged.

Esters can be used, such as those derived from the reaction of acids with $C_1$ to $C_8$ alcohols, and in particular palmitates of secondary alcohols such as isopropanol. By way of example, mention may be made of butyl acetate.

Of course, the liquid phase can be based on a mixture of two or more hydrocarbons or compounds of the type described above.

The suspensions of the invention have an overall oxide content, i.e. cerium oxide content, which can vary within wide limits and which can, for example, be at most 40%, in particular at most 25% to 30% by mass of oxide.

Similarly, the pH of these suspensions can be within a broad range. Thus, the pH of the suspensions derived from the preparation processes that will be described below is generally between 2 and 6, more particularly between 2 and 5, the suspensions remaining stable within the meaning given here below, within this pH range. However the stability can be improved either within these ranges of pH either beyond the value of 5 or 6 in a known manner, by addition to the suspension of compounds such as anionic or zwitterionic polymers or molecules. As compounds of this kind one can mention those compounds obtained by polymerizing at least one monomer chosen among the following: an ethylenically unsaturated, linear or branched, aliphatic, cyclic or aromatic monocarboxylic or polycarboxylic acid or anhydride. Polyacrylic acid or citric acid may be mentioned as examples.

Finally, it will be noted that the suspensions of the invention are stable. This is intended to mean that no formation of a settling cake is observed on these suspensions before several days, for example at least 8 days. Furthermore, the settling cake, if it forms, can be resuspended by simple agitation.

A process for preparing the suspension of the invention will now be described.

The suspension of the invention can be prepared by means of a process which comprises the following steps:
- (a) a solution of a cerium III salt which also comprises a colloidal dispersion of cerium IV is prepared;
- (b) this solution is brought into contact with a base, under an inert atmosphere, by virtue of which procedure a precipitate is obtained;
- (c) the medium obtained in the preceding step is subjected to a thermal treatment under an inert atmosphere, at least one of steps (a), (b) or (c) being carried out in the presence of nitrate ions;
- (d) an acidification and a washing of the medium thus obtained are carried out successively but in any order, by virtue of which procedure the suspension is obtained.

The first step (a) of the process above therefore consists in preparing a starting solution which is a solution of a cerium III salt.

As cerium III salts, use may more particularly be made of cerium III nitrate, chloride, sulphate or carbonate, and also mixtures of these salts, such as mixed nitrates/chlorides.

In the known manner, this starting solution should have the acidity suitable for the cerium to be entirely present in solution.

The starting solution also comprises cerium IV.

This cerium IV is provided by a colloidal dispersion of this element.

The expression "colloidal dispersion of cerium IV" is intended to mean any system constituted of fine solid particles of colloidal dimensions, based in particular on compounds of cerium oxide and/or oxide hydrate (hydroxide) type, in suspension in an aqueous liquid phase, it being possible for said particles to also optionally contain bonded or adsorbed ions such as, for example, nitrates and ammoniums.

Use is preferably made of dispersions of which the particle size is at most 20 nm, more particularly at most 10 nm. The sizes given here should be understood as denoting the mean hydrodynamic diameter of the particles, as determined on the dispersion by quasielastic light scattering (QELS) according to the method described by Michael L. McConnell in the review Analytical Chemistry 53, No. 8, 1007 A, (1981).

Such dispersions are well known; mention may in particular be made of those described in EP 206906 A1, EP 208580 A1, EP 208581 A1, EP 433133 A1 or EP 1265815 A1.

Generally, the amount of cerium IV is such that the (Ce IV/total Ce) molar ratio in the starting solution is between 1/5000 and 1/500, more particularly between 1/4000 and 1/2000.

The starting solution prepared in step (a) can be degassed beforehand by bubbling with an inert gas. The term "inert gas" or "inert atmosphere" is intended to mean, for the present description, an atmosphere or a gas free of oxygen, it being possible for the gas to be, for example, nitrogen or argon.

The second step (b) of the process consists in reacting the starting solution with a base.

Products of the hydroxide type can in particular be used as base. Mention may be made of alkali metal or alkaline-earth metal hydroxides and aqueous ammonia. Secondary, tertiary or quaternary amines can also be used. However, the amines and the aqueous ammonia may be preferred since they reduce the risks of pollution by alkali metal cations or alkaline-earth metal cations.

The base can also be degassed beforehand by bubbling with an inert gas.

To perform the reaction of the second step of the process, the bringing into contact can be carried out in any order of introducing the reactants. However, it is preferable to introduce the starting solution into a medium containing the base.

The second step should be carried out under an inert atmosphere, either in a closed reactor or in a semi-closed reactor with sweeping with the inert gas. The bringing into contact is generally carried out in a stirred reactor.

Finally, this second step is generally carried out at ambient temperature (20° C.-25° C.) or a temperature of at most 50° C.

The third step (c) of the process is a thermal treatment of the reaction medium obtained at the end of the preceding step.

This treatment consists in heating the medium and in maintaining it at a temperature which is generally at most 95° C., and more particularly between 60° C. and 95° C.

The duration of this treatment can be between a few minutes and a few hours.

This treatment is also carried out under an inert atmosphere, the description with respect to this atmosphere for the second step being applied similarly here. Similarly the treatment is carried out in a stirred reactor.

According to one characteristic of the process of the invention, at least one of steps (a), (b) or (c) should be carried out in the presence of nitrate ions. These nitrate ions can be provided by the addition of nitric acid, more particularly in step (a), during the preparation of the cerium III solution, or else by using, in step (a), a cerium nitrate as cerium III salt.

The amount of nitrate ions, expressed by the $NO_3^-/Ce^{3+}$ molar ratio, is generally between ⅓ and 5.

The last step of the process, step (d), in fact comprises two successive operations which can be carried out in any order. These operations are, firstly, an acidification and, secondly, a wash.

These operations will be described more specifically below, for the case of a series in which acidification is followed by washing.

The acidification is generally carried out, after cooling of the medium obtained at the end of step (c), by the addition of an acid.

Any inorganic or organic acid can be used. Nitric acid is more particularly used.

The amount of acid added is such that the pH of the medium after acidification is between 2 and 5.

This operation can be carried out either under air or under an inert atmosphere.

The acidification is followed by washing, the aim of which is to remove from the suspension the soluble species, essentially salts.

The washing can be carried out in various ways with or without solid/liquid separation.

It can thus be carried out by separating the solid particles from the liquid phase, for example by frontal filtration, settling out or centrifugation. The solid obtained is then resuspended in an aqueous phase. The process can also be carried out by tangential filtration.

This washing can be optionally repeated if necessary, for example until a given conductivity of the suspension is obtained, whereby the conductivity measures the amount of impurities present in this suspension.

As indicated above, the order of the operations can be reversed compared with that which has just been described. Thus, at the end of step (c), and, here again, generally after cooling of the medium obtained, washing can then carried out in the manner described above. At the end of the washing, the acidification of the medium obtained is then carried out.

At the end of the steps which have been described, it is possible to treat the suspension which has been obtained in a known deagglomeration apparatus such as an apparatus of ultrasonic treatment, of double impact jet treatment or a wet milling apparatus.

A suspension according to the invention is obtained at the end of step (d).

In the case of a suspension partially or completely in an organic solvent medium other than water, this suspension can be prepared, in a manner known per se, from an aqueous suspension as obtained by means of the process which has just been described and by bringing into contact with the organic solvent.

At this stage, it may be advantageous to add to the organic phase a promoter agent whose function is to accelerate the transfer of the particles from the aqueous phase to the organic phase and to improve the stability of the organic suspensions obtained.

As a promoter agent, use may be made of compounds comprising an alcohol function, and most particularly linear or branched aliphatic alcohols having from 6 to 12 carbon atoms. As specific examples, mention may be made of 2-ethylhexanol, decanol, dodecanol, or mixtures thereof.

The bringing into contact can be carried out at ambient temperature, for example approximately 20° C., but also at a higher temperature, for example in a range of from 60° C. to 150° C.

The separation between the aqueous and organic phases is carried out, for example, by distillation, by settling out or by centrifugation depending on the nature of the organic solvent.

The invention also relates to a redispersible powder of cerium oxide particles. It is a characteristic of this powder that, after introduction into a liquid phase and redispersion in a liquid phase, it produces a suspension according to the invention as described above. The redispersion is carried out by simple agitation of the powder in the liquid phase.

This powder can be obtained from a suspension according to the invention by drying and then calcination at a temperature which may be, for example, at most 300° C., and in particular between 100° C. and 200° C., over a period which can range between a few minutes and a few hours.

The invention also relates to a suspension for polishing, comprising either a suspension as described above, or a suspension as obtained by means of the processes described above, or else a suspension obtained after redispersion of a powder according to the invention. This suspension can be used for polishing glass, for example in the crystal-making or mirror industry, flat glass, television screens or spectacles, or else for polishing ceramics or other materials of vitreous type. This suspension can also be used most particularly for CMP-type polishing in the electronics industry and therefore for polishing metal substrates which go to make up microprocessors, but also for polishing insulating layers of these same microprocessors, the suspension of the invention being particularly suitable for the polishing of said layers. These layers are generally made of silica (doped silica, porous silica).

In general, such suspensions comprise, in addition to the compound with abrasive property, such as the cerium oxide particles, additives such as a dispersing agent or an oxidant.

As other applications of the suspensions of the invention, mention may be made of catalysis, in particular for automobile post-combustion; in this case, the suspensions are used in the preparation of catalysts. The suspensions can also be used for their anti-UV properties, for example in the preparation of films of polymers (of the acrylic or polycarbonate type, for example), of paints, of papers or of cosmetic compositions, in particular in the preparation of anti-UV creams.

Examples will now be given.

EXAMPLE 1

A starting solution is prepared by adding 830.6 g of a 2.88 M trivalent cerium nitrate solution (d=1.715) and 740 mg of a 0.70 M colloidal solution of cerium oxide (d=1.115) of which the particle size measured by QELS is 6 nm. This solution, which has a $Ce^{4+}/Ce_{total}$ molar ratio of 1/3000, is loaded into a semi-closed reservoir and then degassed with vigorous agitation and with nitrogen bubbling for 2 hours.

A dilute solution of aqueous ammonia is prepared by adding 5041.0 g of deionized water and a solution of 423.9 g of 28% aqueous ammonia. This solution is loaded into a semi-closed 6 l jacketed reactor and then subjected to agitation and nitrogen bubbling for 2 hours.

The previously prepared starting solution is then added, at ambient temperature, to the dilute aqueous ammonia solution over 30 min, with agitation and under nitrogen sweeping.

The temperature of the reaction mixture is then increased to 85° C. in ¾ hour and then maintained at this temperature for 4 h, still under nitrogen sweeping.

At the end of this heat treatment, the reaction mixture is left to cool and is then acidified to pH 4 by adding 68% nitric acid. The nitrogen sweeping is stopped and the suspension is finally washed by centrifugation, elimination of the centrifugation water and resuspension of the cake in deionized water. Several cycles of washing by centrifugation are carried out until a suspension, which is finally adjusted to 35 wt % with respect to $CeO_2$ and which has a pH of 5 and an ionic conductivity of 0.2 mS/cm, is obtained. The suspension is deagglomerated by successive passes through a dual-impact jet homogenizer.

The suspension is observed by TEM. On a photograph of several hundred particles representative of the suspension, each of the particles is counted and measured, by virtue of which an average size of 125 nm is obtained, with a standard deviation of 24 nm that is 19% of said average size.

Part of the suspension is dried in an incubator at 250° C., which makes it possible to obtain a $CeO_2$ powder. The X-ray diffractogram of this powder has the signature of crystalline $CeO_2$ (sheet ASTM 34-394).

The BET specific surface area determined by a nitrogen adsorption is 15 m²/g, which gives an average size of the primary particles of 55 nm.

The ratio of the average size measured by TEM to the average size measured by BET is 2.2.

The size of the secondary particles is measured using a Horiba LA910 laser particle sizer, taking a value of 1.7 for the optical index of $CeO_2$ in water. The median size $d_{50}$ is 115 nm. The dispersion index σ/m calculated from the $d_{10}$, $d_{50}$ and $d_{90}$ values of 93, 115 and 146 nm, respectively, is 0.2.

FIG. 1 is a TEM photograph of the suspension obtained in Example 1.

EXAMPLE 2

The suspension as obtained in Example 1 is diluted to 20% by weight with respect to $CeO_2$ by adding deionized water. 100 g of this solution are added, with stirring, to 100 g of a solution of polyacrylic acid (PAA) having a molar mass Mw=2000 g/mol, diluted such that the final $PAA/CeO_2$ ratio is 1.2% by weight. The pH of the suspension thus obtained is brought back up to 8 by adding 28% aqueous ammonia.

The size of the secondary particles is measured using a Horiba LA910 laser particle sizer, taking a value of 1.7 for the optical index of $CeO_2$ in water. The median size $d_{50}$ is 112 nm. The dispersion index σ/m calculated from the $d_{10}$, $d_{50}$ and $d_{90}$ values of 93, 112 and 140 nm, respectively, is 0.2.

COMPARATIVE EXAMPLE

A dilute cerium nitrate solution is prepared by adding 6.4 kg of a 2.88 M trivalent cerium nitrate solution (d=1.715), 1.0 kg of a 68% $HNO_3$ solution, 4.8 kg of deionized water and 8.87 g of 1.39 M tetravalent cerium nitrate (d=1.440). This solution, which has a $Ce^{4+}/Ce_{total}$ molar ratio of 1/1250, is loaded into a semi-closed reservoir and then degassed with vigorous agitation and with nitrogen bubbling for 2 hours.

A dilute aqueous ammonia solution is prepared by adding 22.6 kg of deionized water and a solution of 4.6 kg of 28% aqueous ammonia. This solution is loaded into a semi-closed 40 l jacketed reactor and then subjected to agitation and nitrogen bubbling for 2 hours.

The dilute cerium nitrate solution is then added, at ambient temperature, to the dilute aqueous ammonia solution in 30 min, with agitation and under nitrogen sweeping.

The temperature of the reaction mixture is then increased to 83° C. in ¾ hour and then maintained at this temperature for 4 h, still under nitrogen sweeping.

At the end of this heat treatment, the reaction mixture is left to cool and is then acidified to pH 2 by adding 68% nitric acid. The nitrogen sweeping is stopped and the suspension is finally washed by centrifugation, elimination of the centrifugation water and resuspension of the cake in deionized water. Several cycles of washing by centrifugation are carried out until a suspension, which is finally adjusted to 10 wt % with respect to $CeO_2$ and which has a pH of 3.2 and an ionic conductivity of 0.38 mS/cm, is obtained.

The suspension is observed by TEM. On a photograph of several hundred particles representative of the suspension, each of the particles is counted and measured, by virtue of which an average size of 65 nm is obtained, with a standard deviation of 5.9 nm that is 9% of said average size.

A part of the suspension is dried in an incubator at 200° C., which makes it possible to obtain a $CeO_2$ powder. The X-ray diffractogram of this powder has the signature of crystalline $CeO_2$ (sheet ASTM 34-394).

The BET specific surface area determined by a nitrogen adsorption is 13 m²/g, which gives an average size of the primary particles of 64 nm.

The ratio of the average size measured by TEM to the average size measured by BET is 1.0.

The size of the secondary particles is measured using a Horiba LA910 laser particle sizer, taking a value of 1.7 for the optical index of $CeO_2$ in water. The median size $d_{50}$ is 112 nm. The dispersion index $\sigma/m$ calculated from the $d_{10}$, $d_{50}$ and $d_{90}$ values of 84, 112 and 157 nm, respectively, is 0.32.

Figure 2:
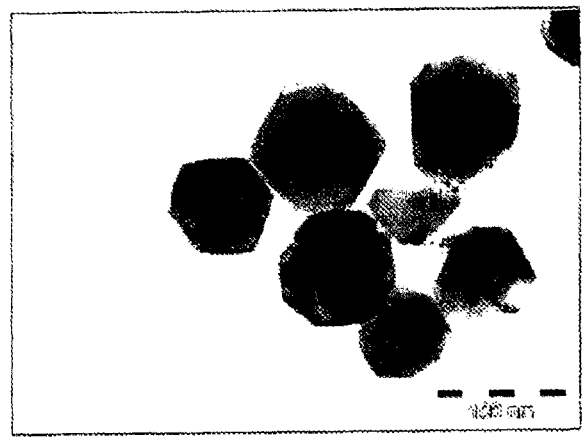
FIG. 2 is a TEM photograph of a suspension according to the prior art.

FIG. 2 is a TEM photograph of the suspension obtained in this comparative example.

The invention claimed is:

1. A process for preparing a cerium oxide suspension comprising the following steps:
   (a) providing a solution of a cerium III salt which also comprises a colloidal dispersion of cerium IV, wherein cerium IV is cerium oxide and/or cerium oxide hydrate;
   (b) contacting this solution with a base, under an inert atmosphere, whereby a precipitate is obtained;
   (c) subjecting the medium obtained in the preceding step to a thermal treatment under an inert atmosphere, at least one of steps (a), (b) or (c) being carried out in the presence of nitrate ions; and
   (d) acidifying and washing the medium thus obtained carried out successively but in any order, whereby the suspension is obtained,
   wherein the suspension comprises monodisperse cerium oxide particles in a liquid phase, the particles (secondary particles) of which have an average size of at most 200 nm, such secondary particles comprising primary particles whose average size measured by TEM is at most 150 nm with a standard deviation of at most 30% of the value of said average size, and for which the ratio of the average size measured by TEM to the average size measured by BET is at least 1.5.

2. The process as defined by claim 1, wherein the solution of a cerium III salt of step (a) comprises cerium IV in a cerium IV/total cerium molar proportion of from 1/5000 to 1/500.

3. The process as defined by claim 1, wherein the content of nitrate ions during at least one of steps (a), (b) or (c), expressed by the $NO_3^-/CE^{3+}$ molar ratio, ranges from ⅓ to 5.

4. The process as defined by claim 1, wherein the thermal treatment is carried out at a temperature of at most 95° C.

5. The process for preparing a cerium oxide suspension as defined by claim 1, wherein the suspension comprises an organic solvent.

* * * * *